United States Patent [19]

Caris et al.

[11] Patent Number: 5,217,873
[45] Date of Patent: * Jun. 8, 1993

[54] TIME-STABLE LIQUID CHOLESTEROL ASSAY COMPOSITIONS

[75] Inventors: Karen R. Caris, Camarillo, Calif.; Ivan E. Modrovich, 1043 Mesa Dr., Camarillo, Calif. 93010

[73] Assignee: Ivan Endre Modrovich, Camarillo, Calif.

[*] Notice: The portion of the term of this patent subsequent to Sep. 10, 2008 has been disclaimed.

[21] Appl. No.: 756,444

[22] Filed: Sep. 9, 1991

Related U.S. Application Data

[63] Continuation of Ser. No. 294,896, Jan. 3, 1989, Pat. No. 5,047,327, which is a continuation of Ser. No. 110,091, Oct. 14, 1987, abandoned, which is a continuation of Ser. No. 868,892, May 27, 1986, abandoned, which is a continuation of Ser. No. 590,220, Mar. 16, 1984, abandoned, which is a continuation of Ser. No. 364,899, Apr. 2, 1982, abandoned.

[51] Int. Cl.$^5$ .............................................. C12Q 1/60
[52] U.S. Cl. .......................................... 435/11; 435/28
[58] Field of Search ................................... 435/11, 28

[56] References Cited

U.S. PATENT DOCUMENTS 4,116,773  9/1978  Polito .................................... 435/11

Primary Examiner—Sam Rosen
Attorney, Agent, or Firm—Christie, Parker & Hale

[57] ABSTRACT

There is provided a stable cholesterol assay composition which comprises an aqueous solution of at least one bile acid or salt thereof being present in an amount of up to about 5 mM; a nonionic surfactant present in an amount of from about 0.15 to about 1.5 percent volume by volume; a buffer in a concentration of from 0 to about 65 mM; and cholesterol oxidase in a concentration of at least about 0.1 KIU/l. Solution pH is from about 5.5 to about 8.5. Addition of cholesterol esterase, phenol, peroxidase and 4-aminoantipyrine provides a total cholesterol chromogen system.

18 Claims, No Drawings

TIME-STABLE LIQUID CHOLESTEROL ASSAY COMPOSITIONS

CROSS-REFERENCE TO RELATED APPLICATIONS

This application is a continuation of application Ser. No. 07/294,896 filed on Jan. 3, 1989 now U.S. Pat. No. 5,047,327 which application is a continuation of Ser. No. 07/110,091 filed on Oct. 14, 1987 (abandoned), which is a continuation of Ser. No. 06/868,892 filed on May 27, 1986 (abandoned), which is a continuation of Ser. No. 06/590,220 filed on Mar. 16, 1984 (abandoned), which is a continuation of Ser. No. 06/364,899 filed on Apr. 2, 1982 (abandoned).

BACKGROUND OF THE INVENTION

It has been known to determine cholesterol in sera by the use of assay compositions based on cholesterol oxidase, presently from a microbial source. The reaction involved is:

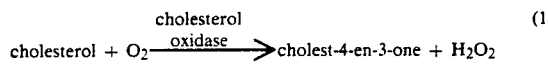

$$\text{cholesterol} + O_2 \xrightarrow{\text{cholesterol oxidase}} \text{cholest-4-en-3-one} + H_2O_2 \quad (1)$$

For total cholesterol determination, bound cholesterol may be released by the inclusion of cholesterol esterase which yields cholesterol by the reaction:

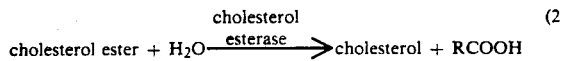

$$\text{cholesterol ester} + H_2O \xrightarrow{\text{cholesterol esterase}} \text{cholesterol} + RCOOH \quad (2)$$

The amount of cholesterol can be assayed by measuring the amount of oxygen consumed, the amount of cholest-4-en-3-one formed, or the amount of hydrogen peroxide formed. A preferred way is to determine the amount of hydrogen peroxide formed by use of a chromogen system. A preferred chromogen system is one based on the presence of peroxidase from a horseradish source, phenol and antipyrine involving the reaction:

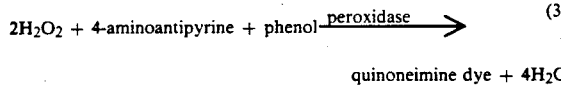

$$2H_2O_2 + \text{4-aminoantipyrine} + \text{phenol} \xrightarrow{\text{peroxidase}} \text{quinoneimine dye} + 4H_2O \quad (3)$$

While most assay systems based on cholesterol oxidase can be made functional as prepared, they are prone to rapid degradation. As a consequence, the art early on lyophilized (freeze-dried) the composition for reconstitution at the time of use. Liapholization is expensive and suffers from inaccuracy.

A need was recognized to provide a liquid assay system of controlled composition which would have an adequate shelf life for marketing purposes. As invented and described by one of us, and disclosed in EPC Application 80.104.568.3, filed Aug. 1, 1980, incorporated herein by reference, it was found that the presence of a material quantity, e.g., up to 50 percent by volume, of a polyhydroxy compound such as glycerol would induce long shelf life to a liquid assay composition. The invention enabled precise quality control to be exercised over the composition of the system, and enabled total reliability of the assay system as a tool. The system was formulated as a concentrate. Shelf life of the concentrate was more than adequate for industrial use and provided levels of stability theretofore unknown in the art.

The polyhydroxy compound, while functional to stabilize the system against degradation, increases costs and, unless proper housekeeping procedures are followed, contaminates apparatus, affecting other tests, particularly triglyceride analysis.

A desire has existed, therefore, for a liquid assay system which did not yield in performance, which could be sold as a single formulation for use as is without dilution and yet have an adequate shelf life to satisfy marketing requirements.

SUMMARY OF THE INVENTION

It has now been found that utilizing basic constituents normally present in a cholesterol assay system, but exercising exacting control over concentration of bile acid or salts thereof, nonionic surfactant and buffer, as well as pH, one can formulate a stable cholesterol assay composition which does not require a polyhydroxy compound and yet exhibits projected shelf lives of 18 months or more at 4° C., and when used with a chromogen system, rapid completion times.

The base solution employed is an aqueous solution of at least one acidic compound which is a bile acid or salt thereof, present in a concentration of up to about 5 mM, preferably from about 0.2 to about 5 mM; a nonionic surfactant, preferably propylene glycol p-isooctylphenyl ether, present in a concentration of from about 0.15 to about 1.5 percent volume by volume, preferably from about 0.2 to about 0.6 percent volume by volume; from 0 to 65 mM of a buffer, preferably from 0.5 to 50 mM, and more preferably from 0.5 to 30 mM, the preferred buffer being potassium dihydrogen phosphate ($KH_2PO_4$); and cholesterol oxidase in a concentration of at least 0.02 KIU/l, preferably at least 0.05 KIU/l, the solution having a pH of from about 5.5 to about 8.5, preferably from 6 to about 7.5.

Where it is desired to assay for total cholesterol, there is included in the composition a microbial cholesterol esterase present in a concentration of at least 0.07 KIU/l, preferably at least about 0.1 KIU/l.

The preferred composition is one containing a chromogen system for determination of hydrogen peroxide. The chromogen system preferably comprises phenol in a concentration of from 8 to about 35 mM; 4-aminoantipyrine in a and peroxidase in a concentration sufficient to enable completion of a chromogen reaction, i.e., development of the pink quinoneimine dye to an intensity quantitative to hydrogen peroxide formed. For commercial practicality, they are provided in quantities sufficient to enable completion of the reaction within 10 minutes at 37° C. Preferably, the peroxidase is provided in a concentration of at least 30 KIU/l, and 4-aminoantipyrine to a concentration of about 0.3 mM.

There is preferably included in the composition a bacteriocide, with the preferred bacteriocide being 2,4 dichlorophenol, present in a concentration of up to about 1 mM, preferably from about 0.4 to about 0.6 mM.

The compositions prepared in accordance with the instant invention are stable for at least 3 days at 41° C., which is equivalent to a projected shelf life of 18 months at 4° C. or about 6 months at ambient temperature (25° C.).

When a chromogen system is employed, completion of reaction preferably occurs within 10 minutes or less at 37° C., with a color stability of at least an additional 30 minutes.

The products are prepared by first forming an aqueous solution to which there is provided buffer, bile acid or salts thereof, and surfactant. Phenol, dichlorophenol and 4-aminoantipyrine are added as required. This base composition is adjusted, if required, to an acceptable pH range by addition of a suitable acid or base.

There is separately formed an aqueous solution containing the nonionic surfactant and the enzymes which are added. The base solution and the solution of the enzymes are then combined to form a net solution.

DETAILED DESCRIPTION

According to the present invention there is provided an assay solution for the determination of cholesterol in the liquids, including sera, and which display a protracted shelf life life, i.e., a shelf life of about 18 months or more at 4° C. (refrigeration conditions). Long shelf life is primarily the result of control over concentration of buffer employed.

A stable cholesterol assay composition of the instant invention comprises an aqueous solution of at least one acidic compound which is a bile acid and/or a salt of a bile acid, the total of said acidic compound being present in an amount of up to about 5 mM, preferably from about 0.2 to about 5 mM; a nonionic surfactant present in a concentration of from about 0.15 to about 1.5 percent volume by volume, preferably from about 0.2 to about 0.6 percent volume by volume; a buffer in a concentration of from 0 to about 65 mM, preferably from about 0.5 to about 50 mM; cholesterol oxidase in a concentration of at least about 0.02 KIU/l, preferably at least 0.05 KIU/l, the solution having a pH of from about 5.5 to about 8.5.

For total cholesterol assay there is included microbial cholesterol esterase present in a concentration of at least about 0.07 KIU/l, preferably at least about 0.1 KIU/l.

The preferred cholesterol assay composition includes a chromogen system for determination of hydrogen peroxide.

More particularly, the preferred chromogen cholesterol assay solutions of the instant invention provide, on a perliter basis, phenol in a concentration of from about 8 to about 35 mM, preferably from about 15 to about 20 mM; bile acid and/or a salt of bile in a total amount up to about 5.0 mM, preferably from about 0.2 to about 5 mM; a nonionic surfactant, preferably polyethylene glycol p-isooctylphenyl ether (TRITON X-100), in a concentration of from about 0.15 to about 1.5 percent by volume, preferably from 0.2 to about 0.6 percent volume by volume; a buffer in a concentration of from 0 to 65 mM, preferably from about 0.5 to about 50 mM; cholesterol oxidase in a concentration of at least 0.02 KIU/l; peroxidase, preferably in a concentration of at least about 30 KIU/l; and, if present, cholesterol esterase in a concentration of at least 0.07 KIU/l, preferably at least about 0.1 KIU/l. Peroxidase and 4-aminoantipyrine are provided in an amount sufficient to enable quantitative colormetric determination of the amount of hydrogen peroxide formed from oxidation of cholesterol. It is preferred that this occur within a 10-minute completion time at 37° C. To this end, it is preferred that 4-aminoantipyrine be present in a concentration of about 0.3 mM. An acceptable range is from about 0.2 mM to about 0.35 mM. If too much or too little 4-aminoantipyrine is present, the reaction will not achieve completion, if at all, in the desired time span.

It is preferred to include in the system a bacteriocide. The preferred bacteriocide is dichlorophenol, and may be provided in a concentration of up to 0.75 mM, preferably from about 0.4 to about 0.5 mM.

The buffer is provided as required, and can be inorganic or organic in nature. Phosphates are preferred. The presently preferred buffer is potassium dihydrogen phosphate ($KH_2PO_4$).

The preferred acidic compound is cholic acid or a metal salt thereof. The presently preferred compound is sodium cholate.

The chromogen cholesterol assay compositions of the instant invention display the ability to recover, i.e., detect, cholesterol; and preferably provide an assay completion time within 10 minutes at 37° C. to a pink color, the developed intensity of which is stable for at least 30 additional minutes. The compositions have a projected stability of at least 18 months at 4° C., or a shelf life of about 6 months at room temperature, as determined by a requirement that they are stable for at least 3 days at 41° C. The chromogen assay systems of the invention are used as such and do not require dilution.

In the chromogen cholesterol assay compositions of the instant invention, a lower level of phenol concentration defines the point at which the system will lose stability, and the upper concentration defines the point at which phenol has reached a concentration where there may be an adverse effect upon color.

Besides being functional as a bacteriocide, dichlorophenol may help speed color development, and therefore is a highly desirable constituent, independent of its bacteriocide function.

The upper level of buffer concentration is critical. If the concentration is too high, completion time will be too slow, giving unreliable results and, quite unexpectedly, there will be an adverse effect on shelf life.

A bile acid or a bile salt is essential. In the absence thereof, the system fails to recover cholesterol. By contrast, at a concentration above about 5 mM, completion times are too long for commercial utility.

The nonionic surfactant has been observed to activate the enzymes, particularly cholesterol esterase. In its absence, reaction time is too long, and if present in too high a concentration will result in foaming and may have an adverse effect on viscosity.

The cholesterol oxidase used in the practice of this invention is currently of a microbial nature. The presently utilized cholesterol oxidase is that manufactured and sold by Whatman Biochemicals, Inc., of England. It has been observed that cholesterol oxidase of the Brevi bacterium is non-functional. Cholesterol esterase is from any microbial source, and that used is manufactured and sold by Kyowa Hakko Kogyo Company, Ltd., of Japan, understood to be produced from the microorganism pseudomonas fluorescens, ATCC 1126. The peroxidase used is, conveniently, horseradish peroxidase.

The products are prepared by first forming an aqueous solution to which there is provided buffer, bile acid or salts thereof, and surfactant. Phenol, dichlorophenol and 4-aminoantipyrine are added as required. This base composition is adjusted, if required, to an acceptable pH range by addition of a suitable acid or base.

There is separately formed an aqueous solution containing the nonionic surfactant and the enzymes which are added. The base solution and the solution of the enzymes are then combined to form a net solution.

The following is the presently preferred chromogen composition, based on the total volume of 1 liter:

| Component | Concentration |
| --- | --- |
| Phenol | 17 mM |
| $KH_2PO_4$ | 12.5 mM |
| 2,4 dichlorophenol | 0.49 mM |
| 4-aminoantipyrine | 0.295 mM |
| Cholic acid | 2.3 mM |
| Cholesterol oxidase | 0.05 KIU/l |
| Cholesterol esterase | 0.1 KIU/l |
| Peroxidase | 30 KIU/l |
| Triton X-100 | 0.4 ± .2 v/v |

Without limiting, the following Examples and Controls illustrate the various parameters associated with the compositions of the instant invention.

EXAMPLE 1

There was formulated a cholesterol assay system by forming a clear base solution of the following composition:

| Component | Concentration |
| --- | --- |
| Water (triple-distilled deionized) | 0.955 liter |
| Triton X-100 (10% v/v solution) | 32.0 ml |
| $KH_2PO_4$ | 12.5 mM |
| 2,4 dichlorophenol | 0.49 mM |
| 4-aminoantipyrine | 0.3 mM |
| Phenol | 17.0 mM |
| Sodium Cholate | 2.3 mM |
| pH | 7.0 |

A clear enzyme solution was formed by addition to 10 ml of an aqueous solution containing Triton X-100, sufficient cholesterol oxidase to provide cholesterol oxidase in a net solution of 0.1 KIU/l, cholesterol esterase in an amount sufficient to provide in the net solution a cholesterol esterase concentration of 0.2 KIU/l, and peroxidase in an amount sufficient to provide in the net solution peroxidase in a concentration of 30 KIU/l.

The enzyme solution was combined with the base solution. The solution recovered cholesterol in an assay with less than a 10-minute completion time at 37° C. The color formed had a stability of greater than 30 minutes, and had a lifetime of in excess of 3 days at 41° C., which is an equivalent of a shelf life of 18 months at 4° C. and about 6 months at room temperature.

Detailed studies were made of variations of the assay composition prepared according to Example 1. The parameters varied were buffer concentration, pH, cholic acid concentration and nonionic detergent concentration. For purposes of all Examples and Controls, the following meanings or codes universally apply:

1 = No change $A_i'$ = Initial absorbence at 500 nm at 37° C. must be less than or equal to 0.15 for a pass 2 = A control manufactured and sold by Beckman Instruments, Inc. that is specific to cholesterol 3 = Mean or principle assigned value (PAV) to the control times 1 or the factor shown 4 = Lot number of Control 5 = A control manufactured and sold by Beckman Instruments, Inc. for multiple assay, including cholesterol 6 = A cholesterol control manufactured and sold by New England Reagent Laboratories. Cholesterol concentration was 200 mg/dl T = TRITON X-100 = a polyethylene glycol p-isooctylphenyl ether having an average formula of $C_{34}H_{62}O_{11}$ and a formula weight of 646, manufactured and sold by Eastman Chemicals Completion times are for Beckman references at a cholesterol concentration of 600 mg/dl.

Color stability is for a cholesterol concentration of 50 mg/dl (low) and/or 500 mg/dl (high). Numerical value given is % change at the time stated.

One or more of the following constitutes failure:

a) no recovery (detection) of cholesterol;

b) greater than 10 minutes completion time at 37° C.; this is failure on the basis that longer completion times are commercially unacceptable;

c) color stability for less than 30 minutes beyond completion time; and/or d) stability for less than three days at 41° C. (stressed).

Failure is also considered to occur if initial absorbent $A_i'$ is greater than 0.15 and cholesterol recovery (level detected) is not within ±5% of sample.

EXAMPLES 2-7 AND CONTROLS A-C

Buffer Concentration

The solution, formulated in accordance with Example 1, was modified in respect of $KH_2PO_4$ concentration. All other constituents were kept constant.

Table I compares performance as formulated (fresh) and after stressed by being heated to 41° C. for the time specified in the Table. Controls A, B and C failed because of long completion times after stress.

TABLE I

| Example or Control | Reagent Condition | pH | Color Stability Low | Color Stability High | Buffer Concentration mM/L | Completion Time Minutes | $A_i'$ |
| --- | --- | --- | --- | --- | --- | --- | --- |
| Example 2 | Fresh | | 0[1] | 2.2% | 0.0 | 3 | .008 |
| | 82 hrs. at 41° C. | | | | | 6 | .028 |
| Example 3 | Fresh | | 0 | 4.0% | 1.0 | 3 | .008 |
| | 82 hrs. at 41° C. | | | | | 7 | .028 |
| Example 4 | Fresh | | 0 | 2.2% | 5.0 | 3 | .008 |
| | 82 hrs. at 41° C. | | | | | 7 | .031 |
| Example 5 | Fresh | | 0 | 1.5% | 12.5 | 3 | .008 |
| | 82 hrs. at 41° C. | | | | | 7 | .035 |
| Example 6 | Fresh | ↑ | 0 | 0 | 25.0 | 3 | .008 |
| | 82 hrs. at 41° C. | ALL ~7.0 ↓ | | | | 8.5 | .038 |
| Example 7 | Fresh | | 0 | 0 | 50.0 | 3 | .008 |
| | 82 hrs. at | | | | | 8.5 | .040 |

TABLE I-continued

| | | | | | | | |
|---|---|---|---|---|---|---|---|
| Control A | Fresh | — | — | 75.0 | 3 | .008 | |
| | 82 hrs. at 41° C. | | | | 15 | .045 | |
| Control B | Fresh | — | — | 100.0 | 5 | .008 | |
| | 48 hrs. at 41° C. | | | | 13 | .038 | |
| Control C | Fresh | — | — | 200.0 | 4–5 | .008 | |
| | 48 hrs. at 41° C. | | | | 25 | .053 | |

| Example or Control | Reagent Condition | 2.5X Beckman Reference[2] 587.5 C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
|---|---|---|---|---|---|---|---|
| Example 2 | Fresh | — | — | — | — | — | — |
| | 82 hrs. at 41° C. | 615 | 144 | 144 | 229 | 427 | 630 |
| Example 3 | Fresh | 604 | 133 | 146 | 225 | 452 | 647 |
| | 82 hrs. at 41° C. | 603 | 137 | 144 | 225 | 440 | 646 |
| Example 4 | Fresh | 593 | 131 | 142 | 224 | 442 | 653 |
| | 82 hrs. at 41° C. | 599 | 133 | 145 | 220 | 442 | 654 |
| Example 5 | Fresh | 590 | 130 | 144 | 222 | 443 | 652 |
| | 82 hrs. at 41° C. | 598 | 132 | 144 | 222 | 441 | 653 |
| Example 6 | Fresh | 589 | 131 | 143 | 222 | 441 | 643 |
| | 82 hrs. at 41° C. | 604 | 132 | 144 | 222 | 439 | 652 |
| Example 7 | Fresh | 588 | 131 | 146 | 222 | 442 | 652 |
| | 82 hrs. at 41° C. | 609 | 130 | 144 | 220 | 439 | 659 |
| Control A | Fresh | | | | | | |
| | 82 hrs. at 41° C. | | | | | | |
| Control B | Fresh | | | | | | |
| | 48 hrs. at 41° C. | | | | | | |
| Control C | Fresh | | | | | | |
| | 48 hrs. at 41° C. | | | | | | |

EXAMPLES 8, 9 and Controls D-I

Evaluation of pH

Using the assay solution prepared according to Example 1, pH was changed using HCl or NaOH to determine its effect on performance. Using the same references of Examples 2-7, the results are shown in Table II.

Failures were due to too long a completion time. Controls D, H and I failed as prepared. Controls E and F failed after stressed for 48 hours, while Control G failed after stressed after 82 hours. Color stability was after 45 minutes.

TABLE II

| Example or Control | Reagent Condition | pH | Color Stability Low | Color Stability High | Completion Time Minutes | A/ | Beckman Reference[2] 2.5X C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
|---|---|---|---|---|---|---|---|---|---|---|---|---|
| Control D | Fresh | 3.5 | | | 14 | .008 | | | | | | |
| Control E | Fresh | 4.0 | | | 10 | .008 | | | | | | |
| | 48 hrs. at 41° C. | | | | >30 | .188 | | | | | | |
| Control F | Fresh | 5.0 | | | 9¾ | .008 | | | | | | |
| | 48 hrs. at 41° C. | | | | FAIL | .072 | | | | | | |
| Example 8 | Fresh | 6.0 | 0 | 0 | 3½ | .008 | 592 | 131 | 148 | 225 | 450 | 667 |
| | 48 hrs. at 41° C. | | | | 5 | .026 | | | | | | |
| | 82 hrs. at 41° C. | | | | 7½ | .036 | 593 | 134 | 149 | 229 | 453 | 674 |
| Example 9 | Fresh | 7.0 | 3.5% | 0 | 3 | .008 | 589 | 130 | 143 | 222 | 441 | 655 |
| | 48 hrs. at 41° C. | | | | 5 | .024 | | | | | | |
| | 82 hrs. at 41° C. | | | | 6½–7 | .032 | 594 | 127 | 145 | 226 | | 661 |
| Control G | Fresh | 8.0 | | | 5¾ | .008 | | | | | | |
| | 48 hrs. at 41° C. | | | | 7 | .046 | | | | | | |
| | 82 hrs. at 41° C. | | | | 11 | .065 | | | | | | |

TABLE II-continued

| Example or Control | Reagent Condition | pH | Color Stability Low | Color Stability High | Completion Time Minutes | $A_i$ | Beckman Reference[2] 2.5X C-011044[4] | Decision I[5] 125[3] C-007014[4] | Decision II[5] 139[3] C-104032[4] | Decision III[5] 211[3] C-007016[4] | 2X Decision III[5] 422[3] | 3X Decision III[5] 633[3] |
|---|---|---|---|---|---|---|---|---|---|---|---|---|
| Control H | Fresh | 9.0 | | | >16 | .008 | | | | | | |
| Control I | Fresh | 9.5 | | | >15 | .008 | | | | | | |

EXAMPLES 10–14 AND CONTROLS J, K

Cholic Acid Effect

Using the assay composition of Example 1, cholic acid concentration was varied, with all other factors kept constant. The results are shown in Table III. Control J failed because the system was turbid, and collapsed when applied to human sera. Control K failed because completion time in human sera was too long, even on stress of the solution by heating to 41° C. for 72 hours. Color stability was after 75 minutes at 37° C.

EXAMPLES 15–20 AND CONTROLS L, M

Nonionic Surfactant

Since the enzymes require some nonionic surfactant in (Triton X-100) for initial enzyme stability, "0" in Control L of Table IV means a concentration on a volume basis of 6 parts per 10,000 parts. Completion times for non-sera were at a cholesterol concentration of 567.5 mg/dl. Cholesterol concentration of the sera used for sera completion time was 650 mg/dl. Control L failed because of too long a completion time in sera.

TABLE III

| Example or Control | Cholic Acid g/l | Cond. | pH | Color Stability Low | Color Stability High | Completion Time Sera Minutes | Completion Time Minutes | $A_i$ |
|---|---|---|---|---|---|---|---|---|
| Control J | 0.0 | Fresh | | | | | ~5–6 | |
| | | 72 hrs. at 41° C. | | 0 | <1% | (Turbidity) COLLAPSE | 6,6 | .045 |
| Example 10 | 0.1 | Fresh | | | | | | |
| | | 72 hrs. at 41° C. | | | | 7 | 7 | .037 |
| Example 11 | 0.3 | Fresh | | | | | | |
| | | 72 hrs. at 41° C. | | | | 6½ | 6 | .033 |
| Example 12 | 0.75 | Fresh | ↑ ALL 7.0 ↓ | | | | | |
| | | 72 hrs. at 41° C. | | | | 6 | 6 | .032 |
| Example 13 | 1.0 | Fresh | | | | | ~5–6 | |
| | | 72 hrs. at 41° C. | | 0 | <2% | 5 | 7 | .034 |
| Example 14 | 1.5 | Fresh | | | | | | |
| | | 72 hrs. at 41° C. | | | | 5¾ | 7 | .035 |
| Control K | 2.0 | Fresh | | | | | ~6–7 | |
| | | 72 hrs. at 41° C. | | | <1% | 10½ | 8½ | .036 |

| Example or Control | Cholic Acid g/l | Cond. | NERL[6] 200 mg/dl | Decision I[5] 124[3] C-007014[4] | Decision II[5] 134[3] C-104032[4] | 2X Decision III[5] 211[3] C-007016[4] | 3X Decision III[5] 422[3] | Decision III[5] 633[3] |
|---|---|---|---|---|---|---|---|---|
| Control J | 0.0 | Fresh | 200 | | | | | |
| | | 72 hrs. at 41° C. | | 114 | 127 | 192 | 278 | 559 |
| Example 10 | 0.1 | Fresh | | | | | | |
| | | 72 hrs. at 41° C. | | | | | | |
| Example 11 | 0.3 | Fresh | | | | | | |
| | | 72 hrs. at 41° C. | | | | | | |
| Example 12 | 0.75 | Fresh | | | | | | |
| | | 72 hrs. at 41° C. | ↓ | | | | | |
| Example 13 | 1.0 | Fresh | | | | | | |
| | | 72 hrs. at 41° C. | | 122 | 135 | | | |
| Example 14 | 1.5 | Fresh | | | | | | |
| | | 72 hrs. at 41° C. | | | | | | |
| Control K | 2.0 | Fresh | | | | | | |
| | | 72 hrs. at 41° C. | | 123 | 138 | 209 | 411 | 614 |

TABLE VI

| Example | Color Stability | Completion Time Sera | Completion |
|---|---|---|---|

TABLE VI-continued

| or Control | T* | Cond. | pH | Low | High | Minutes | Minutes | A$_i$ |
|---|---|---|---|---|---|---|---|---|
| Control L | 0.0 | Fresh | 7.02 | | | | 7 | |
| | | 72 hrs. at 41° C. | 7.01 | 2% | <1% | 20 | 9 | .031 |
| Control M | 0.11 | Fresh | 7.02 | | | | 7.5 | |
| | | 72 hrs. at 41° C. | 7.01 | 2% | <1% | | 10 | |
| Example 15 | 0.21 | Fresh | 7.02 | | | | 7 | |
| | | 72 hrs. at 41° C. | 7.01 | 2% | <1% | | 9.5 | |
| Example 16 | 0.29 | Fresh | 7.02 | | | | 8 | |
| | | 72 hrs. at 41° C. | 7.01 | 2% | <1% | | 9 | |
| Example 17 | 0.38 | Fresh | | | | 3.5 | 7.5 | |
| | | 72 hrs. at 41° C. | | 0% | <1% | 5.25 | 8, 7.5 | |
| Example 18 | 0.70 | Fresh | 7.02 | | | | 8 | |
| | | 72 hrs. at 41° C. | 7.01 | 0% | <1% | 6.5 | 8, 8.25 | |
| Example 19 | 1.02 | Fresh | 7.02 | | | 3.5 | 8 | |
| | | 72 hrs. at 41° C. | 7.01 | | | | | |
| Example 20 | 1.34 | Fresh | 7.02 | | | | 8 | |
| | | 72 hrs. at 41° C. | 7.01 | | 0% | | | |

| Example or Control | T* | Cond. | NERL 200 mg/dl | 123[3] SERA | Decision I[5] 211[3] C-007014[4] | Decision III[5] III[5] C-007016[4] | 2X Decision III[5] 422[3] | 3X Decision 633[3] |
|---|---|---|---|---|---|---|---|---|
| Control L | 0.0 | Fresh | | | | | | |
| | | 72 hrs. at 41° C. | | 263 | 124 | 209 | 408 | 603 |
| Control M | 0.11 | Fresh | | | | | | |
| | | 72 hrs. at 41° C. | | | | | | |
| Example 15 | 0.21 | Fresh | | | | | | |
| | | 72 hrs. at 41° C. | | | | | | |
| Example 16 | 0.29 | Fresh | | | | | | |
| | | 72 hrs. at 41° C. | | | | | | |
| Example 17 | 0.38 | Fresh | | | | | | |
| | | 72 hrs. at 41° C. | | 250 | 122 | 206 | 407 | 616 |
| Example 18 | 0.70 | Fresh | | | | | | |
| | | 72 hrs. at 41° C. | | 252 | 121 | 206 | 413 | 613 |
| Example 19 | 1.02 | Fresh | | | | | | |
| | | 72 hrs. at 41° C. | | | | | | |
| Example 20 | 1.34 | Fresh | | | | | | |
| | | 72 hrs. at 41° C. | | | | | | |

*Triton X-100 Concentration Percent Volume by Volume

Where, in the above Controls, failure is due to too long a completion time, as opposed to inability to recover cholesterol after stress, it is considered only to define a composition considered to have a commercial lack of utility, as completion time is important. Therefore, the specification of the claims is oriented to a commercial product of short completion times. It will be considered, however, to be in the invention a system having longer completion times, provided they have adequate shelf life.

What is claimed is:

1. A stable cholesterol assay composition which comprises an aqueous solution of:
   (a) at least one acidic compound selected from the group consisting of a bile acid and a salt of a bile acid, the total of said acid compound being present in an amount of up to about 5 mM;
   (b) a nonionic surfactant present in a concentration of from about 0.15 to about 1.5 percent volume by volume;
   (c) a buffer in a concentration of from 0 to about v
   (d) cholesterol oxidase in a concentration of at least about 0.02 KIU/l;
   (e) cholesterol esterase present in a concentration of at least about 0.07 KIU/l; and
   (f) a chromogen system for determination of hydrogen peroxide, said cholesterol assay solution having a pH of from about 5.5 to about 7.5 and a completion time of less than 10 minutes at 37° C.

2. A stable cholesterol assay system as claimed in claim 1 in which the chromogen system comprises phenol in a concentration of from about 8 to about 35 mM, and peroxidase and 4-aminoantipyrine in a concentration sufficient to provide a colormetric quantitative determination of the hydrogen peroxide formed from oxidation of cholesterol.

3. A stable cholesterol assay system as claimed in claim 1 which includes a chromogen system for determining hydrogen peroxide and which comprises phenol in a concentration of from about 8 to about 35 mM, 4-aminoantipyrine in a concentration of from about 0.25 to about 0.35 mM, and peroxidase in a concentration of at least about 30 KIU/l.

4. A stable cholesterol assay composition as claimed in claim 1 which includes a bacteriocide.

5. A stable cholesterol assay composition as claimed in claim 4 in which the bacteriocide is 2,4 dichlorophenol.

6. A stable cholesterol assay composition as claimed in claim 5 which includes 2,4 dichlorophenol in a concentration of up to about 1 mM.

7. A stable cholesterol assay composition as claimed in claim 1 in which the nonionic surfactant is polyethylene glycol p-isooctylphenyl ether.

8. A stable cholesterol assay composition as claimed in claim 5 in which the nonionic surfactant is polyethylene glycol p-isooctylphenyl ether.

9. A stable cholesterol assay composition as claimed in claim 1 in which the buffer is potassium dihydrogen phosphate.

10. A stable cholesterol assay composition as claimed in claim 1 in which the acidic compound is a metal salt of cholic acid.

11. A stable total cholesterol chromogen assay composition comprising an aqueous solution have a pH of from about 6.5 to about 7.5 and comprising:
  (a) phenol in a concentration of from about 8 to about 35 mM;
  (b) a metal salt of cholic acid present in a concentration of from about 0.2 to about 5 mM;
  (c) a nonionic surfactant present in a concentration of from about 0.2 to about 1.5 percent volume by volume;
  (d) a phosphate buffer present in a concentration of from about 0.5 to about 30 mM and sufficient to maintain a pH of from about 6 to about 7.5;
  (e) 4-aminoantipyrine in a concentration up to about 0.3 mM;
  (f) cholesterol esterase present in a concentration of at least about 0.07 KIU/l;
  (g) cholesterol oxidase present in a concentration of at least about 0.02 KIU/l; and
  (h) peroxidase,
the amount of peroxidase and 4-aminoantipyrine being sufficient to enable quantitative determination of the amount of hydrogen peroxide formed from oxidation of cholesterol within 10 minutes at 37° C.

12. A stable total cholesterol chromogen assay composition as claimed in claim 11 in which the buffer is potassium dihydrogen phosphate and pH is from about 6 to about 7.5.

13. A stable total cholesterol chromogen assay composition as claimed in claim 11 in which the nonionic surfactant is present in a concentration of from about 0.2 to about 0.4 percent volume by volume.

14. A stable total cholesterol chromogen assay composition as claimed in claim 13 in which the nonionic surfactant is polyethylene glycol p-isooctylphenyl ether.

15. A stable total cholesterol chromogen assay composition as claimed in claim 11 in which peroxidase is present in a concentration of at least about 30 KIU/l and in which 4-aminoantipyrine is present in a concentration of about 0.3 mM.

16. A stable total cholesterol chromogen assay composition comprising an aqueous solution of:
  a) phenol in a concentration of about 17 mM;
  b) 2,4 dichlorophenol present in a concentration of about 0.5 mM;
  c) a metal salt of cholic acid present in a concentration of up to about 5 mM;
  d) polyethylene glycol p-isooctylphenyl ether present in a concentration of from about 0.2 to about 0.6 percent volume by volume;
  e) $KH_2PO_4$ present in a concentration of about 12.5 mM;
  f) peroxidase present in a concentration of about 30 KIU/l;
  g) cholesterol oxidase present in a concentration of at least about 0.05 KIU/l; and
  h) microbial cholesterol esterase present in a concentration of at least about 0.1 KIU/l,
  i) 4-aminoantipyrene present in concentration of about 0.3 mM, said stable total cholesterol chromogen assay composition having a pH of from about 6.0 to about 7.5.

17. A method of preparing a stable total cholesterol chromogen assay composition comprising forming a base solution and an enzyme solution to form a net solution in which:
  a) the base solution comprises a major amount of water and:
    i) a metal salt of cholic acid in an amount sufficient to be present in the net solution in a concentration of up to about 5 mM;
    ii) 2,4 dichlorophenol in an amount sufficient to be present in the net solution in a concentration of about 0.5 mM;
    iii) phenol in an amount sufficient to be present in the net solution in a concentration of about 17 mM;
    iv) $KH_2PO_4$ in an amount sufficient to be present in the net solution in a concentration of about 12.5 mM;
    v) 4-aminoantipyrine in an amount sufficient to be present in the net solution in a concentration of about 0.3 mM; and
    vi) polyethylene glycol p-isooctylphenyl ether,
  b) the enzyme solution comprises an aqueous solution of polyethylene glycol p-isooctylphenyl ether and:
    i) cholesterol oxidase present in an amount sufficient to be present in the net solution in a concentration of at least about 0.05 KIU/l;
    ii) microbial cholesterol esterase in an amount sufficient to be present in the net solution in a concentration of at least about 0.1 KIU/l; and
    iii) peroxidase in an amount sufficient to be present in the net solution in a concentration of at least about 30 KIU/l,
said net solution having a pH of from about 6.0 to about 7.5 and containing polyethylene glycol p-isooctylphenyl ether present in a concentration of from about 0.2 to about 0.6 percent volume by volume.

18. A method for preparing a stable cholesterol assay solution which comprises forming a base solution and an enzyme solution, then combining the base solution and the enzyme solution to form a net solution, and in which:
  (a) the base solution is formed by dissolving in water:
    (i) at least one acidic compound selected from the group consisting of a bile acid and a salt of a bile acid to provide the total of said acidic compound in the net solution in an amount of up to about 5 mM;

(ii) a nonionic surfactant determined to provide an amount in the net solution a nonionic surfactant concentration of from about 0.15 to about 1.5 percent volume by volume, a buffer in an amount sufficient to provide in the net solution a buffer in a concentration of up to 65 mM;

(b) the enzyme solution being formed by dissolving in water containing a portion of the total nonionic surfactant, cholesterol oxidase in an amount sufficient to provide in the net solution cholesterol oxidase in a concentration of at least about 0.02 KIU/l, cholesterol esterase in an amount sufficient to provide in the net solution cholesterol esterase in a concentration of at least about 0.07 KIU/l, peroxidase, phenol in an amount sufficient to provide in the net solution phenol in a concentration of from about 8 to about 15 mM, and 4-aminoantipyrine, the base solution being adjusted to provide a net solution having a pH of from about 5.5 to about 7.5 and the amount of peroxidase and 4-aminoantipyrine being provided in a sufficient amount for the net solution to enable quantitative colormetric determination of the amount of hydrogen peroxide formed from oxidation of cholesterol within 10 minutes at 37° C.

* * * * *

UNITED STATES PATENT AND TRADEMARK OFFICE
CERTIFICATE OF CORRECTION

PATENT NO. : 5,217,873
DATED : June 8, 1993
INVENTOR(S) : Karen R. Caris; Ivan E. Modrovich It is certified that error appears in the above-indentified patent and that said Letters Patent is hereby corrected as shown below:

Column 1, line 53, change "Liapholization" to
-- Lyophilization --.

Column 3, line 18, change "shelf life life" to
-- shelf life --.
Column 3, line 44, change "perliter" to -- per liter --.
Column 3, line 60, change "colormetric" to
-- colorimetric --.

Column 10, Table III, change the last three headings from:

| 2X | 3X | |
|---|---|---|
| III[5] | Decision | Decision |
| 211[3] | III[5] | III[5] |
| C-007016[4] | 422[3] | 633[3] | to:

| | 2X | 3X |
|---|---|---|
| Decision | Decision | Decision |
| III[5] | III[5] | III[5] |
| 211[3] | 422[3] | 633[3] |
| C-007016[4] | | |

Column 10, line 65, change "TABLE VI" to -- TABLE IV --.
Column 10, line 68, Table [VI] IV, under the last heading "Completion" insert -- Time --.

UNITED STATES PATENT AND TRADEMARK OFFICE
CERTIFICATE OF CORRECTION

PATENT NO. : 5,217,873
DATED : June 8, 1993
INVENTOR(S) : Karen R. Caris; Ivan E. Modrovich It is certified that error appears in the above-indentified patent and that said Letters Patent is hereby corrected as shown below:

Column 11, line 1, change "TABLE VI-continued" to
-- TABLE IV-continued --.

Columns 11,12, Table IV, change the last five headings from:

|      | Decision $I^5$ | Decision $III^5$ | 2X Decision | 3X Decision |
|------|----------------|------------------|-------------|-------------|
|      | $123^3$        | $III^5$          | $III^5$     |             |
|      | $211^3$        |                  |             |             |
| SERA | $C-007014^4$   | $C-007016^4$     | $422^3$     | $633^3$     | to:

|      | Decision $I^5$ | Decision $III^5$ | 2X Decision | 3X Decision |
|------|----------------|------------------|-------------|-------------|
|      | $123^3$        | $211^3$          | $III^5$     | $III^5$     |
| SERA | $C-007014^4$   | $C-007016^4$     | $422^3$     | $633^3$     |

UNITED STATES PATENT AND TRADEMARK OFFICE
CERTIFICATE OF CORRECTION

PATENT NO. : 5,217,873
DATED : June 8, 1993
INVENTOR(S) : Karen R. Caris; Ivan E. Modrovich It is certified that error appears in the above-indentified patent and that said Letters Patent is hereby corrected as shown below:

Column 12, line 49, after "about" change "v" to
-- 65 mM; --.
Column 12, line 62, change "colormetric" to
-- colorimetric --.

Column 13, line 16, change "claim 5" to -- claim 3 --.
Column 13, line 26, change "solution have" to -- solution having --.

Column 16, line 9, change "colormetric" to
-- colorimetric --.

Signed and Sealed this

Tenth Day of May, 1994

Attest:

BRUCE LEHMAN

Attesting Officer   Commissioner of Patents and Trademarks